United States Patent [19]
Ball

[11] 4,024,863
[45] May 24, 1977

[54] HAND RESTRAINING DEVICE

[76] Inventor: Dennis C. Ball, 1403 Beechview Ave., Pittsburgh, Pa. 15216

[22] Filed: Apr. 27, 1976

[21] Appl. No.: 680,786

[52] U.S. Cl. .................................. 128/133; 2/16; 70/16
[51] Int. Cl.² ...................................... A61F 13/00
[58] Field of Search .................. 128/133, 26, 77; 2/16–18; 272/67; 70/16–18

[56] References Cited
UNITED STATES PATENTS

| 557,362 | 3/1896 | Clapp | 2/17 |
| 1,042,344 | 10/1912 | Hedrick | 70/16 |
| 1,053,204 | 2/1913 | Morrison | 128/133 X |
| 2,303,675 | 12/1942 | Berghs | 128/133 |
| 3,185,476 | 5/1965 | Fechner | 2/18 X |
| 3,746,356 | 7/1973 | Shipstad | 2/16 |

*Primary Examiner*—Lawrence W. Trapp
*Attorney, Agent, or Firm*—Robert D. Yeager; Robert DeMajistre

[57] ABSTRACT

A hand restraining device is comprised of two closures permanently attached to each other. Each closure is provided for each hand of the person to be restrained. The individual closure is comprised of two spherical or annular sectors which are relatively rotatable. An aperture is located at the intersection of the two spherical or annular sectors in order that a wrist may traverse the closure. Each closure is of a sufficient volume to enclose a fist. Also, each closure is provided with means to secure the closure in a fixed position.

20 Claims, 11 Drawing Figures

HAND RESTRAINING DEVICE

BACKGROUND OF THE INVENTION

1. Field of the Invention

This invention relates to restraining devices and more particularly to hand restraining devices.

2. Description of the Prior Art

In the course of many societal interactions it becomes necessary for authorities to prevent activities of persons which are detrimental to society and/or themselves. In order to prevent such activities many devices have been utilized to restrict the capability of movement within a confined area along with impeding manual dexterity.

In most instances where hand restraint is necessary, it is desirable to not only restrict hand movement but also to restrain the use of the fingers. For example, handcuffs, which are adjustable wrist bands linked together, are well known for restraining prisoners to restrict hand motion. However, handcuffs do not restrain finger movement and raise a possibility for escape where the prisoner may use a fire arm or similar weapon needing finger dexterity.

Further, hand restraining devices are useful in preventing mental patients from injuring themselves or others. Also hand restraining devices are used to prevent infants from skin scratching, thumb sucking, etc.

Several devices for preventing hand movement along with finger movement have been proposed, exemplary of such devices are those shown in U.S. Pat. Nos. 853,025; 1,047,457; 1,529,456; 2,139,897; and 2,303,675.

In accordance with the present invention a hand restraining device is provided which restricts the use of the fingers as well as the hand.

BRIEF DESCRIPTION OF THE INVENTION

A hand restraining device is comprised of two closures permanently attached to each other, one for each hand of the person to be restrained. The individual closure is comprised of two spherical or annular sectors which are relatively rotatable. An aperture is located at the intersection of the two spherical or annular sectors in order that a wrist may traverse the closure. Each of the closures are of a sufficient volume to enclose a fist. Also each closure is provided with means to secure the closure in a fixed position.

The invention will be further illustrated but is not intended to be limited by the following drawings.

DETAILED DESCRIPTION OF THE DRAWINGS

Figure 1:
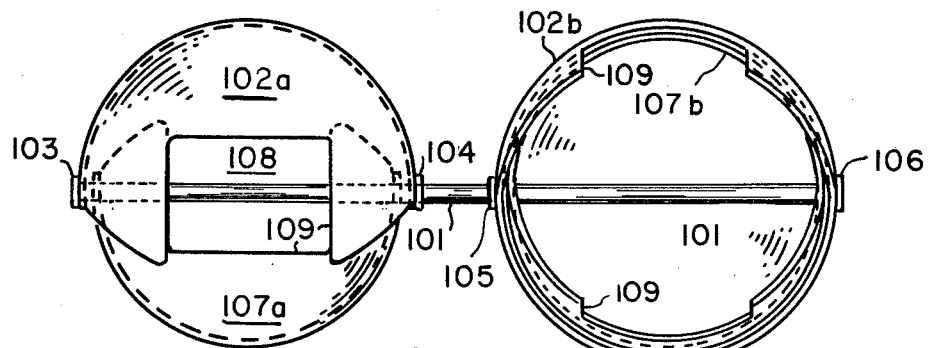
FIG. 1 is a front view of one embodiment of the invention using spherical sectors.
Figure 2:
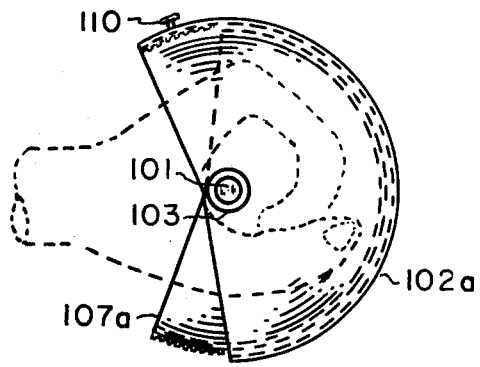
FIG. 2 is a side view of the embodiment of FIG. 1 in open position with a closed fist inserted therein.

In FIGS. 1 through 5 exterior sectors 102a and 102b are axially and rotationally mounted on rigid bar 101. Spherical sectors 102a and 102b are fixed in position along the rigid bar 101 by a series of washers 103, 104, 105 and 106, spot welded thereto. Within and concentric with spherical sectors 102a and 102b are spherical sectors 107a and 107b respectively. The difference between the diameters of sectors 102a and 107a is sufficient so that the sectors freely rotate relative to each other. Most preferably sectors 107a and 107b are welded to rigid bar 101 to provide rotation of sectors 102a and 102b only. This arrangment facilitates the operation of the invention which will be further described.

The spherical sectors 102a, 102b, 107a and 107b are each preferably greater than 180°, however, sectors 102a and 102b can vary in sector arc length from 107a and 107b as long as the added sector arc length of the two sectors providing the closure is greater than 360° and more preferably greater than 410°. This requirement of a total sector arc length of greater than 360° is necessary to provide a complete closure about the hand which is restrained. The total arc length of at least 410° is preferred so that the closure may contain a variety of hand sizes from large to small.

The volume of the closure formed, for example, by sectors 102a and 107a is necessarily limited by the interior diameter of sector 107a. Thus sectors 107a and 107b should be of sufficient volume to contain a large human fist.

Figure 3:
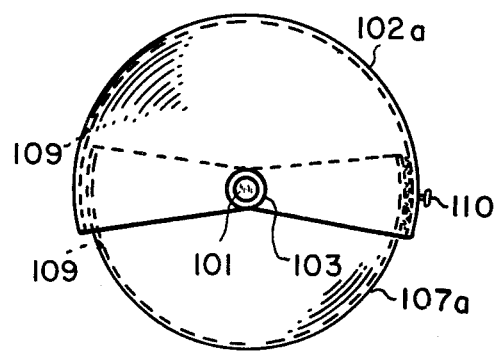
FIG. 3 is a side view of the embodiment of FIG. 1 in closed position.
Figure 4:
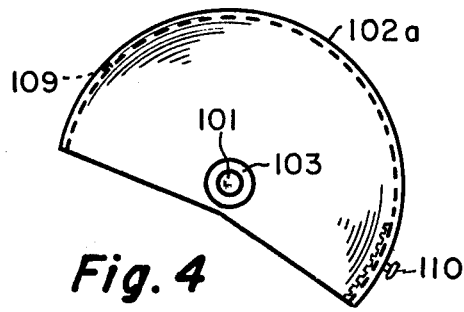
FIGS. 4 and 4A depict the exterior spherical sectors of FIG. 1.
Figure 5:
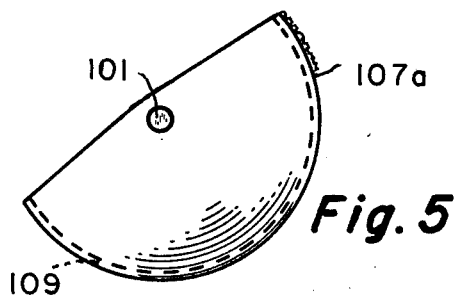
FIGS. 5 and 5A depict the interior spherical sectors of FIG. 1.
Figure 4A:
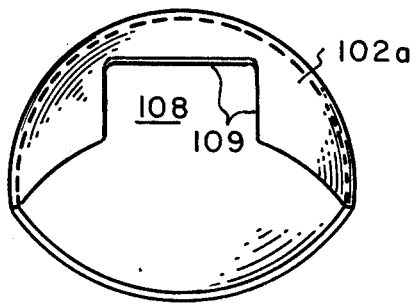
Figure 5A:
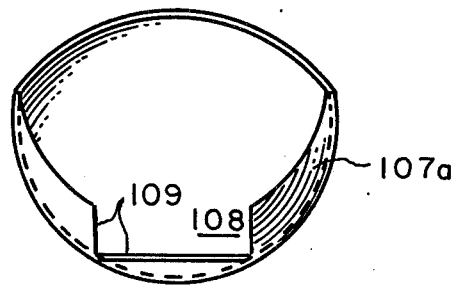

When a closure is provided, as is shown in FIG. 1 and FIG. 3, by sectors 102a and 107a an aperture 108 through the closure is formed. This aperture 108 is variable in a direction perpendicular to the bar 101 depending on the extent to which sectors 102a and 107a are positioned in relation to one another. The variable aperture 108 allows a variety of wrist sizes to traverse the closure while preventing the hand within the closure from being withdrawn therefrom.

Structurally, the aperture for wrist traversal may be provided by a variety of configurations of the spherical sectors. In all embodiments shown herein, the aperture is provided by a rectangular abberation 109 in each spherical sector 102a, 102b, 107a and 107b which diminishes the surface area of each sector.

The spherical sectors 102a and 107a; and 102b and 107b are fixed in position by locking mechanism 110 which is further shown in FIG. 9 to be described hereinafter.

The hand restraining device of all embodiments shown herein can be constructed of metal or plastic. In the case where a metal such as steel is used the component parts to be fixedly mounted may be attached by welding or similar technique. In the case of plastic such as polycarbonate, polyethylene or the like, the apparatus may be injection molded, vacuum formed or produced by similar known techniques.

In operation, the person to be restrained inserts each hand into each of the open spherical sectors. As is shown in FIG. 3, a fist must be formed about the bar 101 because of the restricted volume defined by spherical sectors 107a and 107b. This restricted volume limits finger movement within the closure, when formed, and restrains more effectively than handcuffs.

After the fist is formed within the spherical sectors, the exterior spherical sector, for example, 102a is rotated relatively opposite to spherical sector 107a until the periphery of aberrations 109 in sector 102a and 107a are in close proximity to the wrist thus forming aperture 108 through which the wrist traverses. When the spherical sectors are in the desired position to form the closure they are fixed in position by the locking mechanism.

The process is then repeated for the other hand of the person to be restrained.

For purposes of convenience, spherical sectors 107a and 107b may be permanently mounted to bar 101 so that only sectors 107a and 107b may be rotated. This allows for insertion of the hand to be restrained and subsequent rotation for example of sector 102a only, to form the closure.

Figure 6:
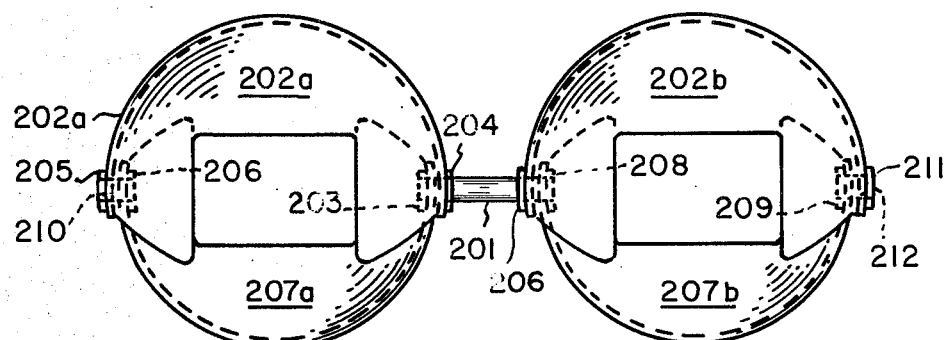
FIG. 6 is a front view of a second embodiment of the invention using spherical sectors.

Referring now to FIG. 6, a second embodiment of the invention is shown. The embodiment of FIG. 6 differs from the embodiment of FIGS. 1 through 5 only in the absence of the bar 101 traversing the interior of the closures. In FIG. 6, spherical sectors 202a, 207a, 202b and 207b are mounted on shaft 201. A washer 203 spot welded to shaft 201 along with spherical sector 202a fixes the position of sector 207a along shaft 201. Spot welded washer 204 on shaft 201 fixes the position of sector 202a along shaft 201. A second shaft 210 provides support and further fixes the position of sectors 202 and 207a in relation to each other by washers 205 and 206 which are welded to second shaft 205.

In like manner, spherical sectors 202b and 207b are mounted to shaft 201 by washers 206 and 208 and also by washers 208 and 211 on third shaft 212.

In operation, the embodiment shown in FIG. 6 functions similar to that shown in FIGS. 1 through 5. A fist is directly inserted, for example, within spherical sector 207a and the closure is formed thereabout.

Figure 7:
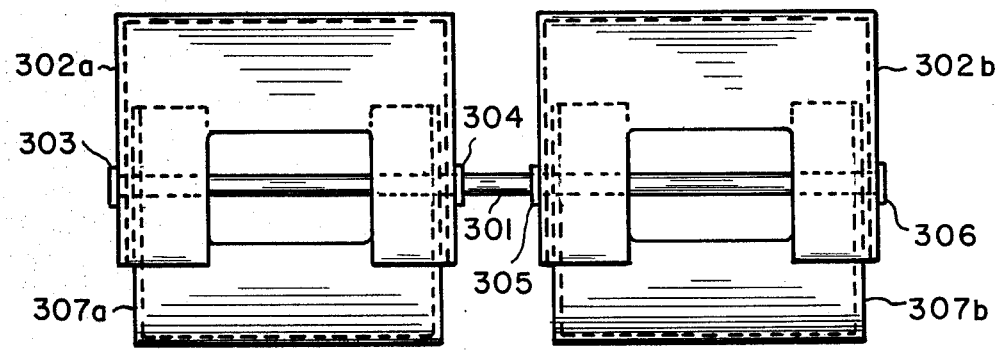
FIG. 7 is a front view of a third embodiment of the invention using annular sectors.

In FIG. 7 a third embodiment of the invention is shown using annular sectors rather than spherical sectors. The principals of construction and operation are similar to those shown in the embodiment of FIGS. 1 through 5. In FIG. 7 exterior annular sectors 302a and 302b are fixed in position along the rigid bar 301 by a series of washers 303, 304, 305 and 306 spot welded thereto. Within and concentric with annular sectors 302a and 302b are annular sectors 307a and 307b respectively. The difference between the diameters of sectors 302a and 307a is sufficient so that the sectors freely rotate relative to each other. Most preferably sectors 307a and 307b are welded to rigid bar 301 to provide rotation of sectors 302a and 302b only. This facilitates the operation of the invention as described previously regarding the embodiment shown in FIGS. 1 through 5.

The annular sectors 302a, 302b, 307a and 307b are each preferably greater than 180°, however, sectors 302a and 302b can vary in arc length from sectors 307a and 307b so long as the added sector arc length of the two sectors providing the closure are greater than 360° and more preferably greater than 410°. This requirement of total sector arc length of greater than 360° is necessary to provide a complete closure about the hand which is restrained.

The volume requirements and wrist traversal provisions of the embodiment shown in FIG. 7 are the same as is described in relation to the embodiment shown in FIGS. 1 through 5.

The operation of the embodiment shown in FIG. 7 is identical to that shown in FIGS. 1 through 5.

Figure 8:
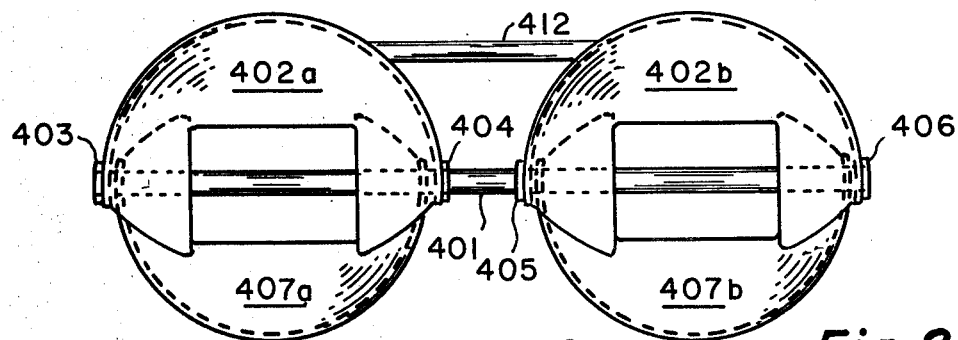
FIG. 8 is a front view of a fourth embodiment of the invention with the outer spherical sectors unitarily rotatable; and, FIG. 9 is a sectional view of the mechanism for fixing the position of the spherical or annular sectors.

Referring now to FIG. 8, a fourth embodiment of the invention is shown which provides for integral movement of the exterior spherical sectors. The device shown in FIG. 8 is identical to that shown in FIGS. 1 through 5 except for the provision of integral movement of the external spherical sectors.

In FIG. 8 exterior sectors 402a and 402b are axially and rotationally mounted on rigid bar 401. Spherical sectors 402a and 402b are fixed in position along the rigid bar 401 by a series of washers 403, 404, 405 and 406 spot welded thereto. Further, the spacing of the pairs of spherical sectors 402a, 407a and 402b, 407b are further provided by rigid member 412 which is fixedly attached to spherical sectors 402a and 402b. Rigid member 412 provides for integral rotation of spherical sectors 402a and 402b about bar 401.

Preferably, the interior spherical sectors 407a and 407b are fixedly mounted to bar 401 by welding or similar technique.

The arc length of the spherical sectors, the means for wrist traversal, the volume of the closure provided and like structural features of the embodiment shown in FIG. 8 are identical to those shown in FIGS. 1 through 5.

In operation, the person to be restrained inserts each hand into each of the open spherical sectors. As is shown similarly in FIG. 3, a fist must be formed about the bar 401 because of the restricted volume within the closure. In this embodiment of the invention both fists must be formed about the bar before the closure can be provided due to the integral movement of exterior spherical sectors 402a and 402b provided by rigid member 412.

After both fists are formed about bar 401, the exterior spherical sectors are integrally rotated to form closures about the fists.

The embodiment shown in FIG. 8 has the advantage of rapid restraint of the hands in that the closures can be simultaneously formed about the fists.

Figure 9:
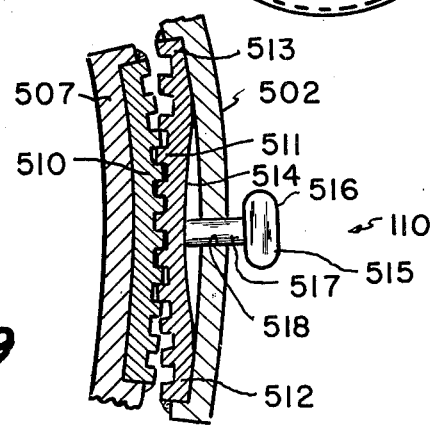

Referring now to FIG. 9, a cross-sectional side view of the spherical or annular sectors 502 and 507 locking mechanism is shown. The embodiments shown in FIGS. 1 through 5, 6 and 7, use two such locking mechanisms, one for each closure. In the embodiment of FIG. 8, only one such locking mechanism is required to fix the position of the closure since the bar 412 maintains the unlocked closure in the same relative position to the internal spherical sector of the unlocked portion as that of the locked closure.

The locking mechanism is formed of one set of teeth 510, mounted on the exterior of the interior sector, which protrude from the outside surface thereof. When the closure is formed for the desired wrist size, a second set of teeth, 511 are proximately alligned with said first set of teeth 510. A sufficient length of the first set of teeth, 510 should be provided for adequate adjustment of the wrist opening. The teeth should be constructed of the same material as the spherical sectors. The teeth 510 are fixedly attached by welding or like technique to sector 507 to remain in a constant position relative to sector 507. Teeth 511 are attached to the interior sector 502 at the lengthwise ends 512 and 513 thereof and are constructed of spring steel or flexible plastic so that the teeth 511 may be flexed in the middle of the teeth strip 514 to protrude from the interior of the periphery of sector 502 and engage teeth 510. When teeth 510 engage teeth 511, the closure is fixed in position. Teeth strip 514 is flexed by key 515 being pushed inwardly by knob 516 which pushes shaft 517 onto strip 514. Shaft 517 is frictionally sealed with aperture 518 in sector 502. Disengagement of teeth 511 or 510 is provided by pulling on knob 516.

Many locking mechanisms useful in the practice of the invention are known to those skilled in the art. The locking mechanism hereinbefore set forth is merely exemplary of one such mechanism.

Although the invention has been described with reference to specific embodiments thereof, the invention is only to be limited as is set forth in the accompanying claims.

What is claimed is:

1. An apparatus for restricting hand movement comprising: two closures, each of said closures comprised of:
    a. a first hollow spherical sector;
    b. a second hollow spherical sector mounted within said first hollow spherical sector to provide for relative rotatable movement of said first and second sectors to provide a closure, said second hollow spherical sector being of sufficient volume to receive the closed fist of a human hand;
    c. an aperture provided at the intersection of the edges of each of said first and second sectors to allow a wrist to traverse the closure while maintaining the fist within the closure;
    d. means for securing said closure by fixing the relative positions of said first and second sectors; and, means for permanently attaching said closures to each other.

2. The apparatus of claim 1 wherein the sum of the arc lengths of said first and second spherical sectors is greater than 360°.

3. The apparatus of claim 1 wherein the sum of the arc lengths of said first and second spherical sectors is greater than 410°.

4. The apparatus of claim 3 wherein the arc lengths of said first and second spherical sectors are equal.

5. The apparatus of claim 1 wherein said first and second spherical sectors are mounted by means of a bar through the axis of said spherical sectors.

6. The apparatus of claim 5 wherein said bar traverses the axis of the spherical sectors of both closures and also provides said means for permanently attaching said closures to each other.

7. The apparatus of claim 1 wherein said aperture is provided by a rectangular aberration in said spherical sectors which diminishes the surface area of said sectors.

8. The apparatus of claim 1 wherein said means for permanently attaching said closures to each other is a bar permanently attached at the axial position of each of said closures.

9. The apparatus of claim 6 wherein said second sector is fixedly mounted to said bar to provide movement of only said first sector with relation to said bar.

10. The apparatus of claim 1 including means for attaching said first hollow spherical sectors to provide unitary movement about their axes.

11. An apparatus for restricting hand movement comprising: two closures, each of said closures comprised of:
    a. a first hollow annular sector;
    b. a second hollow annular sector mounted within said first hollow annular sector to provide for relative rotatable movement of said first and second sectors to provide a closure, said second hollow annular sector being of sufficient volume to receive the closed fist of a human hand;
    c. an aperture provided at the intersection of the edges of each of said first and second sectors to allow a wrist to traverse the closure while maintaining the fist within the closure;
    d. means for securing said closure by fixing the relative positions of said first and second sectors; and, means for permanently attaching said closures to each other.

12. The apparatus of claim 11 wherein the sum of the arc lengths of said first and second annular sectors is greater than 360°.

13. The apparatus of claim 11 wherein the sum of the arc lengths of said first and second annular sectors is greater than 410°.

14. The apparatus of claim 13 wherein the arc lengths of said first and second annular sectors are equal.

15. The apparatus of claim 11 wherein said first and second annular sectors are mounted by means of a bar through the axis of said annular sectors.

16. The apparatus of claim 15 wherein said bar traverses the axis of the annular sectors of both closures and also provides said means for permanently attaching said closures to each other.

17. The apparatus of claim 16 wherein said second sector is fixedly mounted to said bar to provide movement of only said first sector with relation to said bar.

18. The apparatus of claim 11 wherein said aperture is provided by a rectangular aberration in said annular sectors which diminishes the surface area of said sectors.

19. The apparatus of claim 11 wherein said means for permanently attaching said closures to each other is a bar permanently attached at the axial position of each of said closures.

20. The apparatus of claim 11 including means for attaching said first hollow annular sectors to provide unitary movement about their axes.

* * * * *